United States Patent
Nakamura et al.

(10) Patent No.: US 7,358,255 B2
(45) Date of Patent: Apr. 15, 2008

(54) THERAPEUTIC AGENT FOR KERATOCONJUNCTIVAL DISORDER

(75) Inventors: Masatsugu Nakamura, Ikoma (JP); Shin-ichiro Hirai, Ikoma (JP)

(73) Assignee: Santen Pharmaceutical Co., Ltd., Osaka (JP)

( * ) Notice: Subject to any disclaimer, the term of this patent is extended or adjusted under 35 U.S.C. 154(b) by 162 days.

(21) Appl. No.: 10/576,719

(22) PCT Filed: Oct. 22, 2004

(86) PCT No.: PCT/JP2004/016063
§ 371 (c)(1),
(2), (4) Date: Apr. 20, 2006

(87) PCT Pub. No.: WO2005/039574
PCT Pub. Date: May 6, 2005

(65) Prior Publication Data
US 2007/0060628 A1   Mar. 15, 2007

(30) Foreign Application Priority Data
Oct. 24, 2003   (JP)   ............... 2003-364864

(51) Int. Cl.
*A61K 31/427*   (2006.01)
(52) U.S. Cl. .................. 514/259; 514/256; 514/267
(58) Field of Classification Search ................ 514/259, 514/267
See application file for complete search history.

(56) References Cited

U.S. PATENT DOCUMENTS

| | | | |
|---|---|---|---|
| 5,447,946 | A | 9/1995 | Kurono et al. |
| 5,885,997 | A | 3/1999 | Lohray et al. |
| 5,886,014 | A | 3/1999 | Fujita et al. |
| 6,372,750 | B2 | 4/2002 | Lohray et al. |
| 6,573,268 | B1 | 6/2003 | Lohray et al. |
| 6,780,992 | B2 | 8/2004 | Lohray et al. |
| 2007/0093514 | A1 | 4/2007 | Nakamura et al. |

FOREIGN PATENT DOCUMENTS

| | | | |
|---|---|---|---|
| JP | 3-72227 | B2 | 11/1991 |
| JP | 8-231549 | A | 9/1996 |
| JP | 9-295970 | A | 11/1997 |
| JP | 11-130675 | A | 5/1999 |
| JP | 2001-039976 | * | 5/2000 |
| JP | 2001-39976 | A | 2/2001 |
| JP | 2002-515874 | A | 5/2002 |
| JP | 2002-220336 | A | 8/2002 |
| JP | 2002-255854 | A | 9/2002 |
| JP | 2003-509503 | A | 3/2003 |
| WO | WO 97/41097 | A | 11/1997 |
| WO | WO 01/21602 | A1 | 3/2001 |

OTHER PUBLICATIONS

U.S. Appl. No. 10/576,402, filed Apr. 20, 2006; Confirmation No. 2359.
H. Hosoya, Tonyobyosei Kakumakusho, Atarashi Ganka, 13(6), pp. 845-851 (1996).
K. Kameyama, Tonyobyo Gappeisho to shiteno Ganbyohen, Rinsho to Yakubutsu Chiryo, 21(11), pp. 1089-1092 (2002).
Y. Chikama, "Sen'ensei Kakumaku Johi Kasson, Ganka" 43, pp. 1625-1631 (2001).
Japanese Review of Clinical Ophthalmology, 46, pp. 738-743 (1992).
Ophthalmic Surgery, 5, pp. 719-727 (1992).

* cited by examiner

*Primary Examiner*—Michael G. Hartley
*Assistant Examiner*—Jagadishwar Samala
(74) *Attorney, Agent, or Firm*—Frishauf, Holtz, Goodman & Chick, P.C.

(57) ABSTRACT

Object of the present invention is to search a novel pharmaceutical use of 5-[4-(6-methoxy-1-methyl-1H-benzimidazol-2-ylmethoxy)benzyl]thiazolidine-2,4-dione being a condensed heterocyclic compound, or a salt thereof. 5-[4-(6-methoxy-1-methyl-1H-benzimidazol-2-ylmethoxy)benzyl]thiazolidine-2,4-dione or a salt thereof can exert an excellent effect to promote healing in a dry eye model, and is useful as a therapeutic agent for keratoconjunctival disorders such as dry eyes, corneal ulcer, keratitis, conjunctivitis, superficial punctate keratopathy, corneal epithelial defects, conjunctival epithelial defects, keratoconjunctivitis sicca, superior limbic keratoconjunctivitis and filamentary keratitis.

6 Claims, No Drawings

THERAPEUTIC AGENT FOR KERATOCONJUNCTIVAL DISORDER

This application is the United States national phase application of International Application PCT/JP2004/016063 filed Oct. 22, 2004.

TECHNICAL FIELD

The present invention relates to a therapeutic agent for a keratoconjunctival disorder comprising 5-[4-(6-methoxy-1-methyl-1H-benzimidazol-2-ylmethoxy)benzyl]thiazolidine-2,4-dione or a salt thereof as an active ingredient.

BACKGROUND ART

Cornea is a transparent avascular tissue having a diameter of about 1 cm and a thickness of about 1 mm, while conjunctiva is a mucosal membrane covering the eyeball surface posterior to the corneal margin, and the back face of the eyelid. The cornea and the conjunctiva are known to significantly affect the visual function. Keratoconjunctival disorders caused due to a variety of diseases such as corneal ulcer, keratitis, conjunctivitis, dry eyes and the like may adversely affect normal architecture of epithelium, and furthermore, may impair structures and functions of the stroma and endothelium, when the repair of these disorders are retarded, alternatively when these disorders are prolonged without making repair on some grounds. That is because the cornea and the conjunctiva are connected tissues. In these years, with the development of cell biology, factors participating in cell proliferation, migration, adhesion, extension, differentiation and the like had been elucidated, and it was reported that these factors play important roles in repair of corneal disorders (Japanese Review of Clinical Ophthalmology, 46, 738-743 (1992), Ophthalmic Surgery, 5, 719-727 (1992)).

Japanese Patent No. 2976885 discloses that 5-[4-(6-methoxy-1-methyl-1H-benzimidazol-2-ylmethoxy)benzyl]thiazolidine-2,4-dione is effective as a therapeutic agent for diseases resulting from insulin resistance such as diabetes and hyperglycemia, and for inflammatory diseases such as osteoarthritis and rheumatic arthritis, while JP-A Nos. 2001-39976 and 2002-220336 disclose that the hydrochloride of the aforementioned compound exhibits excellent oral absorptivity, as a result of remarkable elevation of solubility in comparison with the free form thereof (the compound without forming a salt).

However, no report has been found in which pharmacological actions of the aforementioned compound on ophthalmic diseases such as keratoconjunctival disorders were studied.

DISCLOSURE OF THE INVENTION

It is a very interesting attempt to search novel pharmaceutical use of 5-[4-(6-methoxy-1-methyl-1H-benzimidazol-2-ylmethoxy)benzyl]thiazolidine-2,4-dione and salts thereof.

The present inventors intensively studied for the purpose of searching novel pharmaceutical use of the aforementioned compound, and found that the aforementioned compound exerts an excellent improving effect on corneal damages in a healing effect test. Thus, the invention was accomplished.

Accordingly, the present invention is directed to a therapeutic agent for keratoconjunctival disorders such as dry eyes, corneal ulcer, keratitis, conjunctivitis, superficial punctate keratopathy, corneal epithelial defects, conjunctival epithelial defects, keratoconjunctivitis sicca, superior limbic keratoconjunctivitis and filamentary keratitis, which comprises 5-[4-(6-methoxy-1-methyl-1H-benzimidazol-2-ylmethoxy)benzyl]thiazolidine-2,4-dione or a salt thereof as an active ingredient.

5-[4-(6-methoxy-1-methyl-1H-benzimidazol-2-ylmethoxy)benzyl]thiazolidine-2,4-dione of the invention (hereinafter, referred to as the "present compound"), is a condensed heterocyclic compound represented by the following chemical structural formula [1]. The salt thereof is not particularly limited as long as it is a pharmaceutically acceptable salt. Examples of the salt include salts with an inorganic acid such as hydrochloric acid, nitric acid or sulfuric acid; salts with an organic acid such as acetic acid, fumaric acid, maleic acid, succinic acid or tartaric acid; and salts with an alkali metal or an alkaline earth metal such as sodium, potassium or calcium. Preferred salt is hydrochloride. Also, quaternary ammonium salts of the present compound are included in the salts according to the invention. Moreover, when there is a geometric isomer or an optical isomer of the present compound, those isomers shall fall within the scope of the invention. The present compound may be in the form of a hydrate or a solvate.

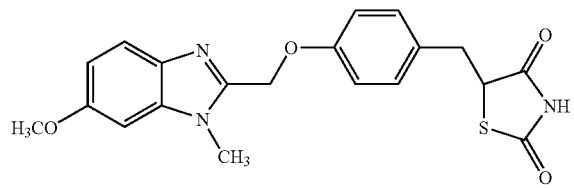

[1]

The keratoconjunctival disorder referred to herein means the state of damaged cornea and/or conjunctiva due to various factors, and examples thereof include dry eyes, corneal ulcer, keratitis, conjunctivitis, superficial punctate keratopathy, corneal epithelial defects, conjunctival epithelial defects, keratoconjunctivitis sicca, superior limbic keratoconjunctivitis, filamentary keratitis and the like.

The therapeutic agent for a keratoconjunctival disorder of the invention may be administered either orally or parenterally. Examples of the dosage form include eye drops, ophthalmic ointments, injections, tablets, capsules, granules, powders and the like. In particular, eye drops are preferred. These can be prepared using any of generally used techniques. For example, the eye drops can be prepared using a tonisity agent such as sodium chloride or concentrated glycerin, a buffer such as sodium phosphate or sodium acetate, a surfactant such as polyoxyethylene sorbitan monooleate, polyoxyl 40 stearate or polyoxyethylene hardened castor oil, a stabilizer such as sodium citrate or sodium edetate, a preservative such as benzalkonium chloride or paraben as needed. The pH is permitted as long as it falls within the range that is acceptable as an ophthalmic preparation, but is preferably in the range of from 4 to 8.

The ophthalmic ointment can be prepared with a generally used base such as white soft paraffin or liquid paraffin. Also, oral preparations such as tablets, capsules, granules and powders can be prepared by adding an expander such as lactose, crystalline cellulose, starch or vegetable oil, a lubricant such as magnesium stearate or talc, a binder such as hydroxypropyl cellulose or polyvinyl pyrrolidone, a disintegrant such as carboxymethyl cellulose calcium or low-substituted hydroxypropylmethyl cellulose, a coating agent such as hydroxypropylmethyl cellulose, macrogol or a silicon resin, a film forming agent such as gelatin film, and the like, as needed.

The invention also relates to a method for treating a keratoconjunctival disorder which comprises administering 5-[4-(6-methoxy-1-methyl-1H-benzimidazol-2-ylmethoxy)benzyl]thiazolidine-2,4-dione or a salt thereof to a patient who requires a treatment of a keratoconjunctival disorder in a therapeutically effective amount.

The dose may be selected appropriately depending on the symptoms, age, dosage form and the like, but in case of the eye drops, they may be administered once or several times per day, in concentration of from 0.0001 to 1% (w/v), preferably from 0.001 to 1% (w/v). Further, in case of the oral preparation, in general, 0.1 to 5000 mg, preferably 1 to 1000 mg of the present compound per day may be administered once or several times in divided doses.

As described later, when a healing effect test for a corneal damage was carried out, the present compound exerted an excellent effect to promote healing in a dry eye model, therefore, the compound is useful as a therapeutic agent for keratoconjunctival disorders such as dry eyes, corneal ulcer, keratitis, conjunctivitis, superficial punctate keratopathy, corneal epithelial defects, conjunctival epithelial defects, keratoconjunctivitis sicca, superior limbic keratoconjunctivitis and filamentary keratitis.

BEST MODE FOR CARRYING OUT THE INVENTION

Hereinafter, Preparation Examples and results of a pharmacological test are demonstrated. These examples are provided for the purpose of better understanding of the invention, but do not restrict the scope of the invention.

PREPARATION EXAMPLE

Typical Preparation Examples containing 5-[4-(6-methoxy-1-methyl-1H-benzimidazol-2-ylmethoxy)benzyl]thiazolidine-2,4-dione (present compound) are shown below.

Preparation Example 1 in 100 ml:

| present compound | 10 mg |
| --- | --- |
| sodium chloride | 900 mg |
| sterile purified water | q. s. |

By altering the amount of addition of the present compound, eye drops having a concentration of 0.001% (w/v), 0.01% (w/v), 0.03% (w/v), 0.1% (w/v), 0.3% (w/v), 1.0% (w/v), 3.0% (w/v) can be prepared.

Preparation Example 2 in 100 ml:

| present compound | 100 mg |
| --- | --- |
| sodium chloride | 800 mg |
| disodium hydrogenphosphate | 100 mg |
| sodium dihydrogenphosphate | q. s. |
| sterile purified water | q. s. |

By altering the amount of addition of the present compound, eye drops having a concentration of 0.1% (w/v), 0.3% (w/v), 0.5% (w/v), 1.5% (w/v), 3% (w/v) can be prepared.

Preparation Example 3 in 100 g:

| present compound | 0.3 g |
| --- | --- |
| liquid paraffin | 10.0 g |
| white petrolatum | q. s. |

By altering the amount of addition of the present compound, ophthalmic ointment having a concentration of 1% (w/w), 3% (w/w) can be prepared.

[Pharmacological Test]

Healing Effect Test for Corneal Damage

Using male SD rats, a dry eye model was produced according to the method of Fujihara et al. (Invest. Ophthalmol. Vis. Sci 42 (1): 96-100 (2001)). After producing the dry eye model, cure rate of a corneal damage was determined according to the method of Miyata et al. (Japanese Review of Clinical Ophthalmology, 48 (2): 183-188 (1994)).

(Test Method)

A male SD rat was systemically anesthetized by an interperitoneal administration of Nembutal in an amount of 35 mg/kg. Subsequently, exorbital lacrimal gland was removed, and corneal damage was induced over two months.

Next, a 0.01% solution of the present compound dissolved in a physiological saline solution was instilled into one eye, while the physiological saline solution (control) was instilled into the other eye, respectively, six times per day for 7 days.

On day 7 after initiating the instillation, impaired part of the cornea was stained with fluorescein. Score of upper, middle and lower parts of the cornea were assessed according to the following criteria on the extent of staining by fluorescein, respectively. Hence, improvement ratio of the corneal damage was calculated from the mean value of total scores on each part described above.

Similar test was also conducted on normal eyes as described above to determine the mean value of total scores on each part described above.

(Criteria of Decision)

0: No punctate staining

1: Scattered staining (punctate, separated staining)

2: Moderate staining (a part of punctate staining being adjacent)

3: Heavy staining (punctate, barely separated staining)

(Results)

Improvement ratio of the 0.01% eye drop administration group of the present compound is shown in Table 1 calculated on the basis of the mean value of total scores of the aforementioned respective parts in the group (control) administered with a physiological saline solution eye drop as a standard value (improvement ratio: 0%), according to the following calculating formula. Mean value of the scores was obtained by averaging 8 examples in each case.

Improvement ratio (%) =

{(control) − (present compound)}/damage degree × 100  Damage degree = (control) − (normal eye)

TABLE 1

| Group | Mean value of total scores | Improvement ratio (%) |
|---|---|---|
| Normal eye | 2.9 | |
| Control | 6.1 | 0 |
| Present compound | 4.4 | 53 |

(Discussion)

As is apparent from the results of the pharmacological test in which the aforementioned rat was used, 5-[4-(6-methoxy-1-methyl-1H-benzimidazol-2-ylmethoxy)benzyl]thiazolidine-2,4-dione markedly improves the corneal damage.

INDUSTRIAL APPLICABILITY

5-[4-(6-methoxy-1-methyl-1H-benzimidazol-2-ylmethoxy)benzyl]thiazolidine-2,4-dione and salts thereof exert an excellent effect to promote healing in a dry eye model, therefore, they exert excellent effects to improve keratoconjunctival disorders such as dry eyes, corneal ulcer, keratitis, conjunctivitis, superficial punctate keratopathy, corneal epithelial defects, conjunctival epithelial defects, keratoconjunctivitis sicca, superior limbic keratoconjunctivitis and filamentary keratitis.

The invention claimed is:

1. A method for treating a keratoconjunctival disorder which comprises administering a therapeutically effective amount of 5-[4-(6-methoxy-1-methyl-1H-benzimidazol-2-ylmethoxy)benzyl]thiazolidine-2,4-dione or a pharmaceutically acceptable salt thereof to a patient in need thereof.

2. The method according to claim 1 wherein said keratoconjunctival disorder is dry eyes, corneal ulcer, keratitis, conjunctivitis, superficial punctate keratopathy, corneal epithelial defects, conjunctival epithelial defects, keratoconjunctivitis sicca, superior limbic keratoconjunctivitis or filamentary keratitis.

3. The method according to claim 1 wherein the administration is instillation of an eye drop.

4. The method according to claim 2 wherein the administration is instillation of an eye drop.

5. The method according to claim 1 wherein the administration is the application of an ophthalmic ointment.

6. The method according to claim 2 wherein the administration is the application of an ophthalmic ointment.

* * * * *